United States Patent

Cook

Patent Number: 6,106,482

Date of Patent: Aug. 22, 2000

[54] REFLEX HAMMER

[75] Inventor: Daniel G. Cook, Maple Plain, Minn.

[73] Assignee: Health & Technology, Inc., Minneapolis, Minn.

[21] Appl. No.: 09/314,989

[22] Filed: May 20, 1999

[51] Int. Cl.[7] .................................................. A61B 19/00
[52] U.S. Cl. .......................................... 600/553; 600/587
[58] Field of Search .................................... 600/552, 553, 600/557, 587; 81/19, 20, 22, 21

[56] References Cited

U.S. PATENT DOCUMENTS

| | | | |
|---|---|---|---|
| 1,267,554 | 5/1918 | Karatsu | 600/553 |
| 3,515,125 | 6/1970 | Ruskin | 600/553 |
| 4,324,261 | 4/1982 | Mark et al. | 600/553 |
| 4,373,565 | 2/1983 | Soto | 81/19 |
| 4,865,045 | 9/1989 | Monreal | 600/553 |
| 5,265,871 | 11/1993 | Hanley | 473/415 |
| 5,372,053 | 12/1994 | Lee | 81/20 |
| 5,588,343 | 12/1996 | Rust et al. | 81/20 |
| 5,657,763 | 8/1997 | Schneider | 600/553 |
| 5,836,891 | 11/1998 | Dimarogonas | 600/552 |

*Primary Examiner*—Eric F. Winakur
*Assistant Examiner*—Charles Marmor, II
*Attorney, Agent, or Firm*—Kinney & Lange, P.A.

[57] ABSTRACT

A reflex hammer having a shaft, a head and a clip. The shaft extends from a neck to a handle and has an inner stiffner encapsulated by a polymeric material body. The polymeric material body extends from the neck of the shaft to form the head. The clip is secured to the reflex hammer along the shaft for securely carrying the reflex hammer.

18 Claims, 4 Drawing Sheets

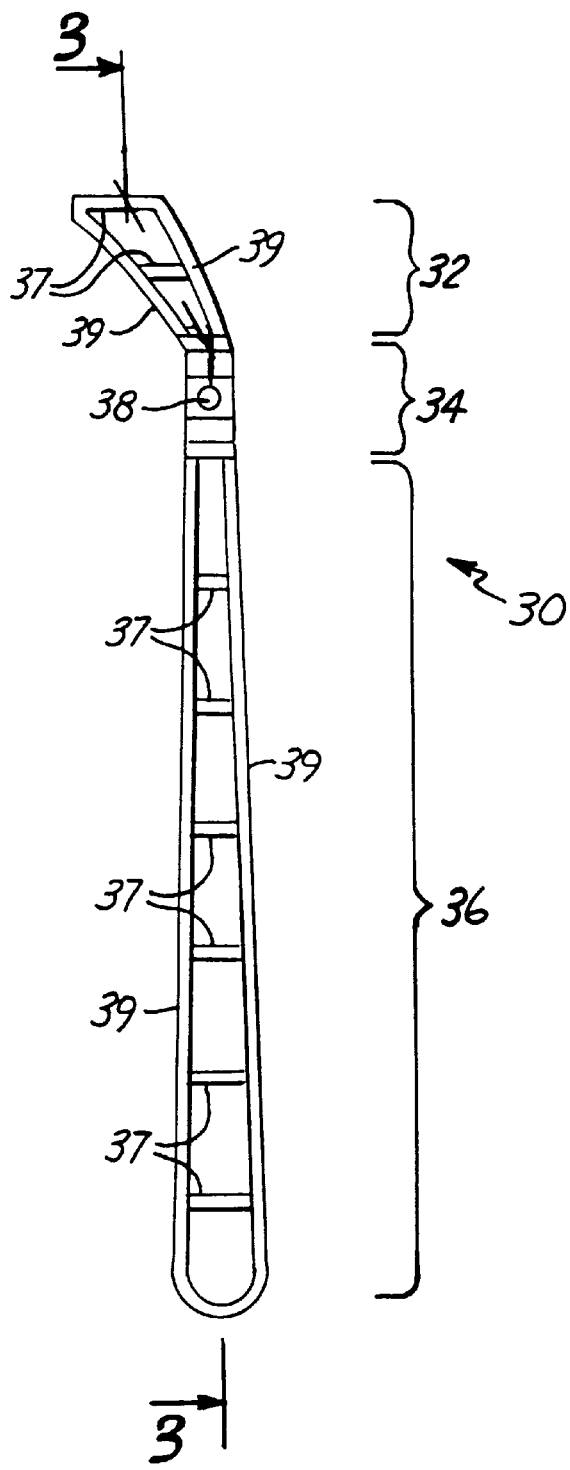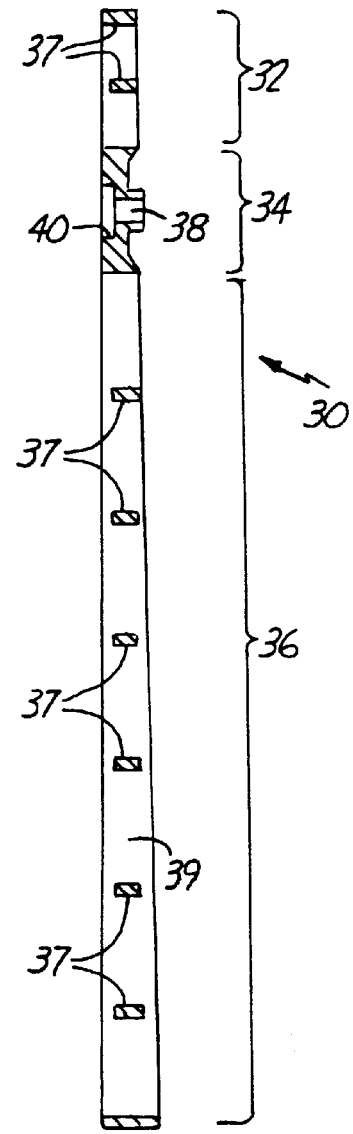
Fig. 2
Fig. 3

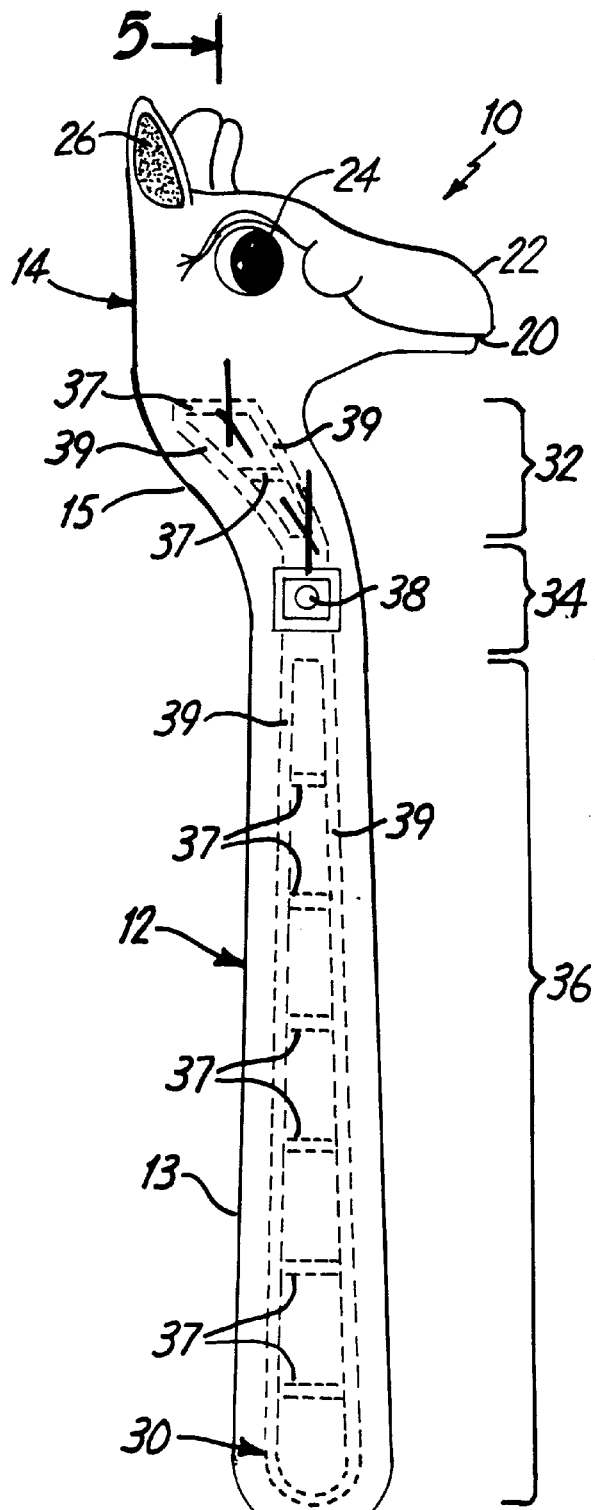
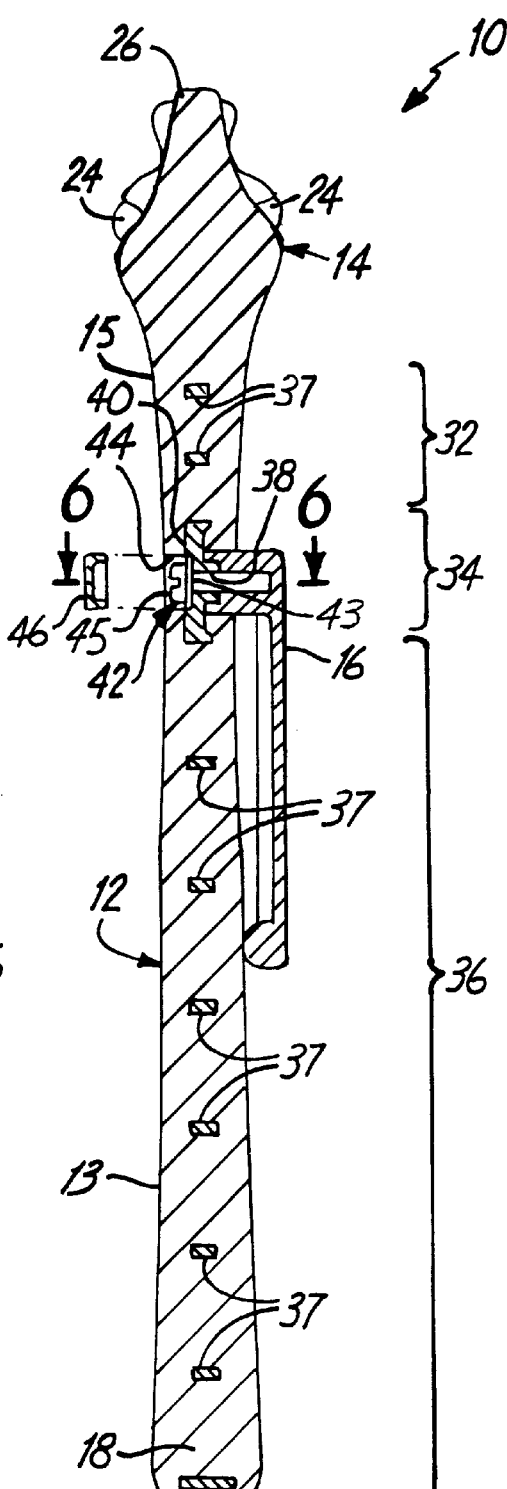

REFLEX HAMMER

BACKGROUND OF THE INVENTION

The present invention pertains to a reflex hammer. More particularly, the invention pertains to a polymeric reflex hammer.

A standard reflex hammer is constructed from a stainless steel shaft with a triangular shaped rubber head at an end of the shaft. The stainless steel shaft is hard and generally silver in color. The triangular rubber head is generally red in color. The standard reflex hammer has been known for many years and has been used during medical evaluations to test an individual's reflexes.

The standard reflex hammer works well for adults and older children. However, younger children are generally intimidated by the standard reflex hammer and react in a manner which inhibits or prevents medical personnel from properly evaluating their reflexes. Medical personnel will sometimes allow the young child to play with or handle the standard reflex hammer in an attempt to allow the child to overcome their fear of the instrument. However, the standard reflex hammer is not suitable for young children to handle or play with.

The shaft of the standard reflex hammer, which is made of stainless steel, is generally cold to the touch. Thus, when the instrument is given to a young child to associate and play with, the child either drops the instrument or refuses to handle it due to the coldness of the shaft. As a result, the child's fear of the instrument is generally increased and the likelihood of evaluating the child's reflexes decreases. The hardness of the stainless steel shaft is also not suitable for children to handle. Children will typically place the instrument into their mouth and bite on it or drop it, either of which could be harmful to the young child. The triangular shaped rubber head is also typically secured to the shaft by forcing half of the head through an eyelet at an end of the shaft. The head can thus become unlodged from the eyelet creating a hazard for young children.

The standard reflex hammer is generally carried loose in the pocket of a smock or examination overcoat. The reflex hammer can fall out of the pocket or become lost. Additionally, if the hammer is left in a pocket and out of the child's sight until it is going to be used, the child may become startled and intimidated by the introduction of the new instrument just prior to its use. The child may react by refusing to allow the medical personnel to use the instrument to test reflexes.

There is a need for a device which is safe and inviting to use with young children to test their reflexes and which can be securely carried.

BRIEF SUMMARY OF THE INVENTION

The invention is a device for testing reflexes of individuals, particularly young children, in a safe and unintimidating manner. The device comprises a shaft, a head and a clip. The shaft includes a handle, a neck and an inner stiffner. The inner stiffner is encapsulated by a polymeric material which forms the handle and the neck and has a hardness rating of about 60 durometer. The head is also formed from polymeric material and is connected to the neck of the shaft. The clip is attached along the shaft to securely carry the device.

BRIEF DESCRIPTION OF THE DRAWINGS

FIG. 2 is a side view of a stiffner used in a preferred embodiment of the invention.

FIG. 3 is a cross sectional view along section 3—3 of FIG. 2.

FIG. 4 is a side view of the preferred embodiment of the invention with a clip removed and the stiffner shown in phantom.

FIG. 5 is a sectional view along section 5—5 of FIG. 4.

DETAILED DESCRIPTION

Figure 1:
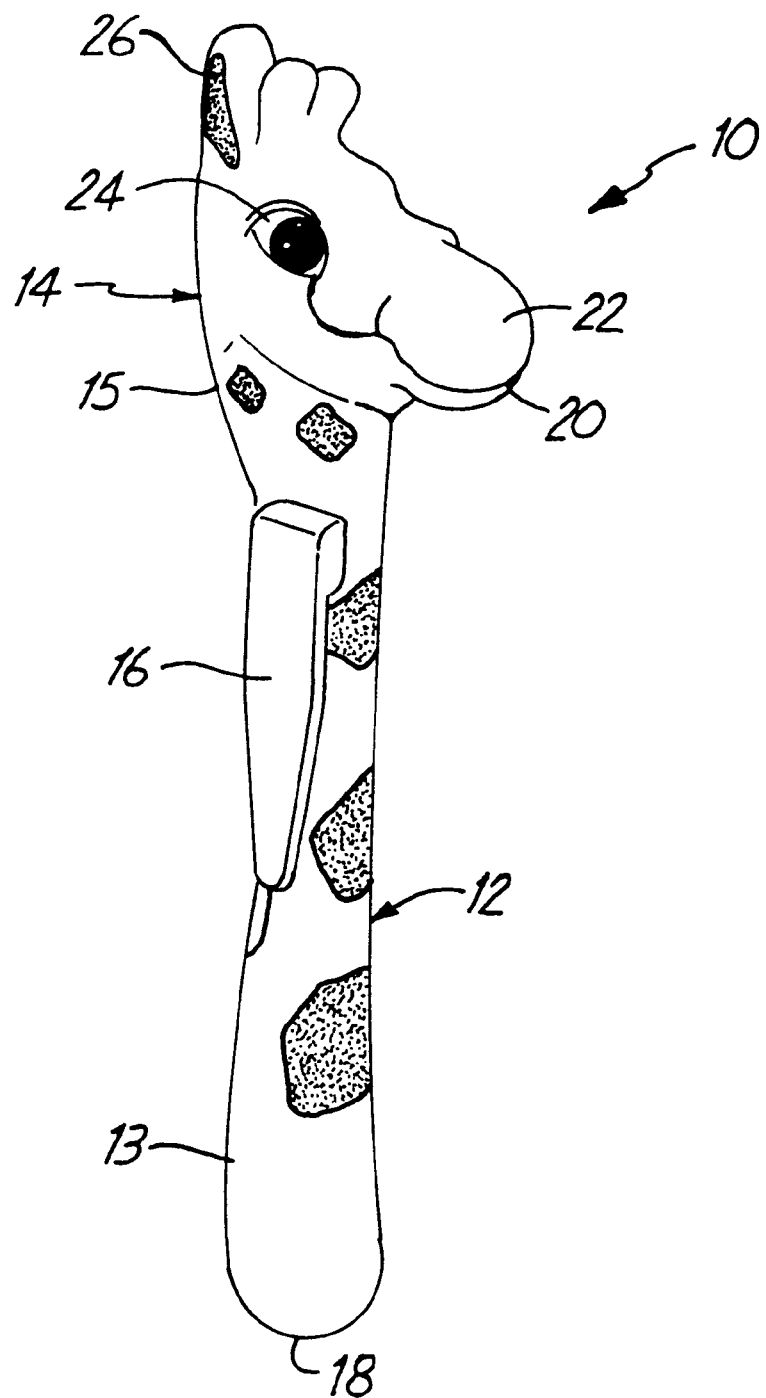
FIG. 1 is a perspective view of a preferred embodiment of the invention.

FIG. 1 is a perspective view of a preferred embodiment of a polymeric reflex hammer 10. The reflex hammer 10 includes a shaft 12, a head 14 and a clip 16. The shaft 12 further includes a handle 13 and a neck 15. The reflex hammer 10 is grasped along the handle 13 and the head 14 is attached to the shaft 12 at the neck 15. The neck 15 preferably angles in a backward direction providing support to the head 14. The shaft 12 and the head 14 are made from a polymeric material, such as polyvinyl chloride (PVC). In a preferred embodiment, the shaft 12 and the head 14 are integrally formed as a molded PVC body 18.

The head 14 has a generally triangular shape and includes facial features of an animal, such as having a mouth 20, a nose 22, a pair of eyes 24, and a pair of ears 26. The color of the PVC body 18 can also be dyed, shaded or painted similar to the color of the animal. In a preferred embodiment, the reflex hammer 10 resembles a giraffe; thus the PVC body 18 is substantially tan or light brown with dark brown spots.

The PVC body 18 preferably has a hardness rating of about 60 durometer. At this rating, the reflex hammer 10 can adequately test and evaluate a patient's reflexes, but yet is soft enough to be handled by a child. Also, the PVC which integrally forms both the shaft 12 and the head 14 of PVC body 18, avoids unsafe situations arising from the head 14 becoming separated from the shaft 12.

PVC also absorbs and retains heat better than stainless steel, which is typically used for a shaft in standard reflex hammers. As a result, if the reflex hammer 10 is given to a child to associate with, the child will be less likely to refuse the reflex hammer 10 because it is warm rather than cold to the touch. The child is therefore more likely to handle the instrument and calm any fears of the reflex hammer 10.

The clip 16 is secured to the reflex hammer 10 along the shaft 12. The clip 16 allows the reflex hammer 10 to be attached to a pocket of a medical smock or overcoat and securely carried. The clip 16 is secured to the reflex hammer 10 so that it opens in a downward direction opposite the head 14 as shown in FIG. 1. In this manner, when the reflex hammer 10 is secured to a pocket, it appears as though the head 14 of the animal is peering out of the pocket and is visible to the young child. By allowing the child to see the reflex hammer 10 prior to its use, and particularly the head 14, the child is more likely to be interested in and want to play with the reflex hammer 10. The child is therefore more likely to allow their reflexes to be tested.

In a preferred embodiment, the reflex hammer 10 has been weighted and balanced to equal that of the standard reflex hammer. The reflex hammer 10 thus accommodates users of the standard reflex hammer so that the two reflex hammers can be used interchangeably with no noticeable difference.

FIG. 2 is a side view of a stiffner 30. The stiffner 30 is located within PVC body 18 along the shaft 12 and into the head 14 to maintain the form of and provide rigidity to the reflex hammer 10. Without the stiffner 30, PVC by itself would be too flexible to maintain its form, and be used to check the reflexes of a patient.

The stiffner 30 has a top section 32, a middle section 34 and a base section 36. The base section 36 extends along a substantial portion of the shaft 12 and primarily along the handle 13 of the reflex hammer 10. The width of the base section 36 increases as it extends downward and away from the middle section 34 and the top section 32. In both the top section 32 and the base section 36, the stiffner 30 is preferably made up of a series of crossbars 37 between a pair of side rails 39. The open architecture of the stiffner 30 allows the PVC body 18 to form around the crossbars 37 and within the side rails 39. This helps ensure the PVC body 18 is formed as a solid mass to securely embed or hold the stiffner 30 without any air pockets.

The middle section 34 of stiffner 30 is preferably positioned between the base section 36 and the top section 32. The middle section 34 includes a through hole 38 that is used to secure the clip 16 to the reflex hammer 10. By placing the middle section 34 near the top section 32, when the reflex hammer 10 is attached to a pocket it will appear as if the head 14 is peering or extending out of the pocket.

The top section 32 extends from the middle section 34 in a direction opposite to the base section 36. The top section 32 extends along the neck 15 of the shaft 12. The top section 32 is preferably angled in a backward direction and provides the transition from the shaft 12 to the head 14 at the neck 15. The top section 32 also provides structural support to the head 14.

FIG. 3 is a sectional view of the stiffner 30 along section 3—3 of FIG. 2. In FIG. 3, the middle section 34 is more clearly shown. As shown in FIG. 3, the through hole 38 includes a recessed section 40 that is formed in the stiffner 30. As shown in FIG. 3, the stiffner 30 is solid throughout the middle section 34, except for the through hole 38. The open architecture of the stiffner 30 in the top section 32 and the base section 36 created by the crossbars 37 between the side rails 39 is also illustrated in FIG. 3.

FIG. 4 is a side view of the reflex hammer 10, with the stiffner 30 shown in phantom and the clip 16 removed. As shown in FIG. 4, the base section 36 of the stiffner 30 is aligned with the handle 13 along the principal portion of the shaft 12. The middle section 34 is placed between the base section 36 and the top section 32. The top section 32 transitions the reflex hammer 10 from the shaft 12 to the head 14 at the neck 15. The side rails 39 in the top section 32 preferably angle in a backward direction to help support the head 14.

FIG. 5 is a sectional view of the reflex hammer 10 along section 5—5 of FIG. 4. As shown in FIG. 5, the clip 16 is secured to a middle section 34 of the stiffner 30. The clip 16 is secured by a screw 42 which is inserted into the through hole 38 in the stiffner 30, and is threadably received into the clip 16. A washer 43 is preferably placed between the screw 42 and the stiffner 30 for a more secure connection to the clip 16. The recess 40 in the stiffner 30, and a recess 44 in the PVC body 18, which is aligned with the recess 40, allows a head 45 of the screw 42 to be secured below the outer surface of the reflex hammer 10 once it is secured to the clip 16. A cap 46 covers the head 45 of the screw 42 providing a continuous outer appearance to the reflex hammer 10. The cap 46 is preferably glued in place to prevent it from falling out and to help prevent the screw 42 from loosening.

Figure 6:
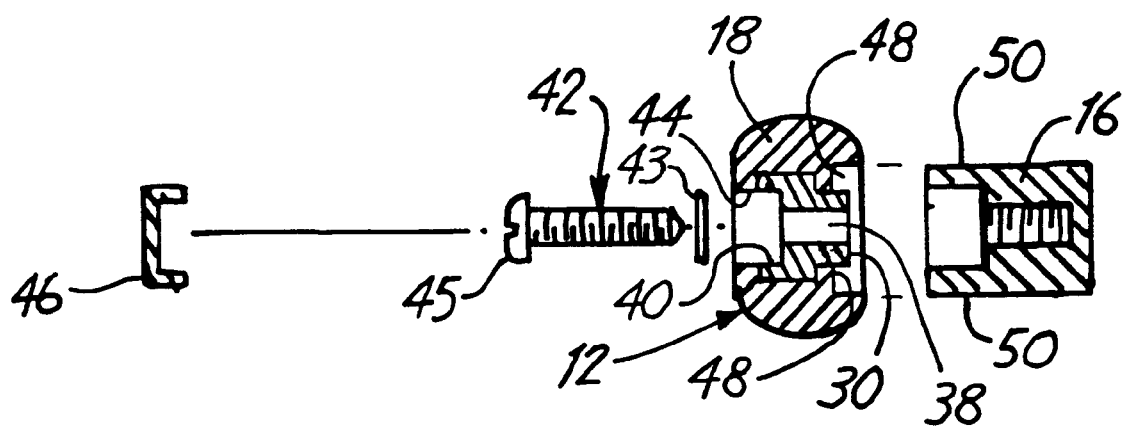
FIG. 6 is an exploded, top sectional view along section 6—6 of FIG. 5.

FIG. 6 is an exploded, sectional view along section 6—6 in FIG. 5. The middle section 34 of the reflex hammer 10 is more clearly shown in FIG. 6. As part of the middle section 34, through hole 38 is shown through the stiffner 30. Encapsulated around the stiffner 30 is the PVC body 18 that forms part of the shaft 12. A cavity 48 is formed between the PVC body 18 and the stiffner 30. The cavity 48 is aligned with and receives an extension 50 on the clip 16. The extension 50 and the cavity 48 help prevent sliding or twisting of the clip 16 once it is aligned and attached to the reflex hammer 10 along the shaft 12. Once the clip 16 is in place, the screw 42 is inserted through the washer 43, into the through hole 38 and is threadably received by the clip 16. The recess 44 allows the head 45 of the screw 42 to be secured beneath the outer surface of the PVC body 18 that forms the shaft 12. The cap 46 is then placed over the head 45 of the screw 42. The outer surface of the reflex hammer 10 thus appears to be continuous in nature.

In a preferred embodiment, the stiffner 30 and the clip 16 are made of nylon 6, a polyamide product produced by duPont. By use of nylon 6, the clip 16 and the reflex hammer 10 can be subjected to severe bending or distortion without breaking and yet still return to their original positions as shown in FIG. 1. Additionally, a clear coat of lacquer is preferably applied to the reflex hammer 10 after the PVC body 18 has been formed over the inner stiffner 30. The lacquer coating covers the PVC body 18, which when formed at the 60 durometer hardness rating may exhibit a sticky feel or touch. The reflex hammer 10 preferably measures approximately 7½ inches long and is approximately 2 inches wide at the head 14, ½ inch wide at the neck 15 and 1 inch wide at the bottom of the handle 13.

Although the present invention has been described with reference to preferred embodiments, workers skilled in the art will recognize that changes may be made in form and detail without departing from the spirit and scope of the invention. For instance, the PVC body 18 could be formed with a somewhat different hardness rating, consistent with the requirements for applying force to a patient's joints to test reflexes. Other polymeric materials can be used in place of PVC. Also, a different material than nylon 6 for the stiffner and clip can be used. Facial features of different animals can be substituted as well. The neck can also be straight or angled in a different direction or to a different degree. The reflex hammer disclosed is thus inviting and safe to use with young children and can be securely carried.

What is claimed is:

1. A reflex hammer comprising:
   a shaft having an inner stiffner encapsulated by a formed body of a polymeric material;
   a head formed from the polymeric material and located at an end of the shaft wherein the head has a generally triangular shape; and
   a clip secured along the shaft.

2. The reflex hammer of claim 1, wherein the clip is secured to the reflex hammer through the inner stiffner of the shaft.

3. The reflex hammer of claim 2, wherein the clip fits into a key way in the inner stiffner, and is secured therein by a screw.

4. The reflex hammer of claim 1, wherein the shaft further includes a neck to which the head is attached and a handle to grasp the reflex hammer.

5. The reflex hammer of claim 1, wherein the inner stiffner is made of nylon 6.

6. The reflex hammer of claim 1, wherein the generally triangular shape of the head includes facial features of an animal.

7. The reflex hammer of claim 1, wherein the polymeric material is polyvinyl chloride.

8. The reflex hammer of claim 1, wherein the polymeric material has a hardness rating of about 60 durometer.

9. A reflex hammer comprising:

an inner stiffner; and a polymeric body which encapsulates the inner stiffner and forms a head and a shaft, the shaft having a handle and a neck, such that the head extends from the neck of the shaft, wherein the head has a generally triangular shape.

10. The reflex hammer of claim 9, wherein a clip is secured to the shaft.

11. The reflex hammer of claim 9, wherein the stiffner is encapsulated in the polymeric body along the shaft from the neck to the handle.

12. The reflex hammer of claim 9, wherein the polymeric material is polyvinyl chloride.

13. The reflex hammer of claim 9, wherein the stiffner is made of nylon 6.

14. The reflex hammer of claim 9, wherein the head includes facial features of an animal.

15. A reflex hammer comprising:

a head formed of polymeric material, wherein the head has a generally triangular shape;

a shaft formed of polymeric material having a neck and a handle, wherein the shaft extends in a downward direction from the neck, which is connected to the head, down to the handle;

a stiffner located within the polymeric material that forms the shaft, wherein the stiffner extends from the handle to the neck; and a clip secured to the shaft.

16. The reflex hammer of claim 15, wherein the head includes facial features of an animal.

17. The reflex hammer of claim 15, wherein the polymeric material is polyvinyl chloride.

18. The reflex hammer of claim 15, wherein the stiffner is made of nylon 6.

* * * * *